US006626029B2

(12) United States Patent
Dunegan (10) Patent No.: US 6,626,029 B2
(45) Date of Patent: Sep. 30, 2003

(54) APPARATUS AND METHODS FOR MEASURING SURFACE ROUGHNESS

(76) Inventor: Harold L. Dunegan, 22812 Tamora Dr., Laguna Niguel, CA (US) 92677

( * ) Notice: Subject to any disclaimer, the term of this patent is extended or adjusted under 35 U.S.C. 154(b) by 0 days.

(21) Appl. No.: 10/114,721

(22) Filed: Apr. 2, 2002

(65) Prior Publication Data

US 2002/0112533 A1 Aug. 22, 2002

Related U.S. Application Data

(63) Continuation of application No. 09/480,714, filed on Jan. 7, 2000, now abandoned.
(60) Provisional application No. 60/115,117, filed on Jan. 8, 1999.

(51) Int. Cl.$^7$ ................................................. G01B 5/28
(52) U.S. Cl. ......................................................... 73/105
(58) Field of Search ................................... 73/104, 105

(56) References Cited

U.S. PATENT DOCUMENTS

| | | | |
|---|---|---|---|
| 3,566,163 A | | 2/1971 | Fischer et al. |
| 3,985,024 A | | 10/1976 | Horak |
| 4,011,472 A | | 3/1977 | Feng |
| 4,036,057 A | | 7/1977 | Morais |
| 4,039,767 A | | 8/1977 | Leschek |
| 4,064,735 A | | 12/1977 | Hutchison et al. |
| 4,088,907 A | | 5/1978 | Jones et al. |
| 4,353,255 A | | 10/1982 | Fukuda et al. |
| 4,535,629 A | | 8/1985 | Prine |
| 4,738,137 A | | 4/1988 | Sugg et al. |
| 4,831,365 A | * | 5/1989 | Thomas et al. ................ 73/104 |
| 5,001,931 A | | 3/1991 | Nishimoto et al. |
| 5,014,556 A | | 5/1991 | Dunegan |

(List continued on next page.)

OTHER PUBLICATIONS

"Non–Destructive Characterization of Hydrogen–Embrittlement Cracking by Acoustic Emission Techniques": H.L. Dunegan and A.S. Tetelman; Engineering Fracture Mechanics. vol. 2., pp. 387–402 (1971).

(List continued on next page.)

*Primary Examiner*—Daniel S. Larkin
(74) *Attorney, Agent, or Firm*—Knobbe, Martens, Olson & Bear LLP (57) ABSTRACT

A method for measuring surface roughness during formation of the surface due to grinding, polishing, and machining operations is described. It is also shown that the same technique can be used to measure the surface roughness after it has been formed. The measurement is accomplished by acoustically coupling a broadband piezoelectric transducer to the surface of the plate being measured by the use of petroleum jelly or other liquids that will eliminate an air interface between the surface to be measured and the transducer. Stress waves are generated in the plate by grinding or polishing operations. These same types of waves are generated by moving an object over a given surface (for example the human finger). Signals received by the transducer are split into two frequency ranges. One part of the signal is hi-pass filtered above 100 KHz, the other part of the signal is band-pass filtered between 20–60 Khz. It is observed that signals from a rough surface have higher amplitudes in the low frequency channel (LF), while signals produced from a smoother surface have higher amplitudes in the high frequency channel (HF). Signals from both frequency channels are amplified and routed to a circuit that measures the average signal level (ASL) from both channels. These ASL signals are then routed to a computer containing an A/D converter. The ratio of the HF/LF amplitudes are then calculated by the computer. It is observed that the value of this ratio can be correlated to the surface roughness generated by the above processes in spite of changes in amplitude of the signal due to velocity effects and instrument gain.

2 Claims, 12 Drawing Sheets

U.S. PATENT DOCUMENTS

| | | | |
|---|---|---|---|
| 5,029,474 A | 7/1991 | Schulze | |
| 5,041,989 A | 8/1991 | Kataoka et al. | 702/39 |
| 5,101,162 A | 3/1992 | Webster et al. | |
| 5,191,558 A | 3/1993 | Gorman et al. | |
| 5,191,796 A | 3/1993 | Kishi et al. | |
| 5,251,469 A | 10/1993 | Chan | |
| 5,270,950 A | 12/1993 | Cowley et al. | |
| 5,635,643 A | 6/1997 | Maji | |
| 5,714,687 A | 2/1998 | Dunegan | 73/587 |
| 5,929,315 A | 7/1999 | Dunegan | 73/1.82 |
| 6,041,656 A | 3/2000 | Dunegan | 73/587 |
| 6,062,083 A | 5/2000 | Dunegan | 73/587 |
| 6,092,412 A * | 7/2000 | Flechsig et al. | 73/105 |
| 6,280,290 B1 | 8/2001 | Birang et al. | |

OTHER PUBLICATIONS

"AE Source Orientation by Plate Wave Analysis"; Michael R. Gorman and William H. Prosser; Journal of Acoustic Emission. vol. 9, No. 4, pp. 283–288 (1991).

"Plate Wave Acoustic Emission"; Michael R. Gorman; J. Acoustics Society of America (Jul. 1991).

"Relating Acoustic Emission Theory to Practice"; Michael R. Gorman; International Advances in Nondestructive Testing; Warren McGonnogle, Editor; Gordon and Breach, Publisher, vol. 17, p. 287 (1992).

"Experimental Far–Field Widebank Acoustic Waves in Wood Rods and Plates"; M.A. Hamstad et al.; Proceedings of the 9th International Symposium on Nondestructive Testing of Wood; Conferences & Institutes, Washington State University (1994).

"Accurate Simulation of Acoustic Emission Sources in Composite Plates"; W.H. Prosser and M.R. Gorman; 1994 ASN Spring Conference (1994).

"The DECI Report"; H.L. Dunegan (Jun. 1995).

"The Use of Plate Wave Analysis in Acoustic Emission Testing to Detect and Measure Crack Growth in Noisy Environments"; H.L. Dunegan; 1996 Structural Materials Technology NDE Conference (1996).

Invention Description, William H. Prosser and Michael R. Gorman, Sep. 1993.

Technical Reports –"Modal Analysis of Acoustic Emission Signals", H.L. Dunegan, Oct. 1997.

RatioAverage vs Grit Size, Sent to potential customer–Nov. 3, 1997.

"Get Smart get the Aesmart 2000 –The Virtual AE Instrument for the $21^{st}$ Century", Dunegan Engineering Consultants, Inc.

"The DECI Report", H.L. Dunegan (Jul. 2, 1998).

"The DECI Report"; H.L. Dunegan (Sep., 1998).

"An Acoustic Emission Technique For Measuring Surface Roughness"; H.L. Dunegan (Dec., 1998).

* cited by examiner

FIGURE 2

Figure 3 - HF Voltage(mv) for three different velocities and 2 surface roughness.

FIGURE 6

HF/LF RATIO FOR TWO SURFACE ROUGHNESS PARALLEL AND PERPENDICULAR TO GROOVES

FIGURE 12

APPARATUS AND METHODS FOR MEASURING SURFACE ROUGHNESS

PRIORITY CLAIM

This application is a continuation of Ser. No. 09/480,714 Jan. 7, 2000 now abandoned and claims benefit 60/115,117 Jan. 8, 1999.

FIELD OF THE INVENTION

This invention relates to the measurement of surface roughness of a material created by grinding, polishing, or machining of the surface, by the use of acoustic emission transducers and instrumentation.

BACKGROUND OF THE INVENTION

A common practice is to attach a high frequency piezoelectric transducer to an object to be measured and record the RMS level of the signal produced by the particular process i.e., grinding, polishing or machining. The amplitude of the RMS signal is the primary measurement tool for correlating the AE signal to a particular parameter created by the process. Such acoustic emission techniques are also used for head disk interference (HDI) measurements by manufacturers of hard disk media for computers. However, major problems are encountered with these techniques. The measurements are very sensitive to the relative velocity between two contacting surfaces of a given roughness, and are effected by the transducer sensitivity and instrument gain.

SUMMARY OF THE INVENTION

Apparatus constructed and methods performed in accordance with the preferred embodiment of this invention have significant advantages. In particular, the accuracy measurements of a surface condition are not adversely effected by velocity effects and instrument gain. The preferred embodiment of the invention uses the ratio between two signals which are determined by averaging two signals that respectively correspond to two frequency components of the signal produced by the transducer to provide a measurement of surface roughness that is substantially insensitive to the amplitude of the transducer output signal.

BRIEF DESCRIPTION OF THE DRAWINGS

The invention will now be described with reference to the appended drawings which depict embodiments of aspects and features of the invention. The illustrated embodiments, however are intended to only illustrate and not to limit the invention.

The drawings contain the following figures.

DETAILED DESCRIPTION OF THE PREFERRED EMBODIMENT

Figure 1:
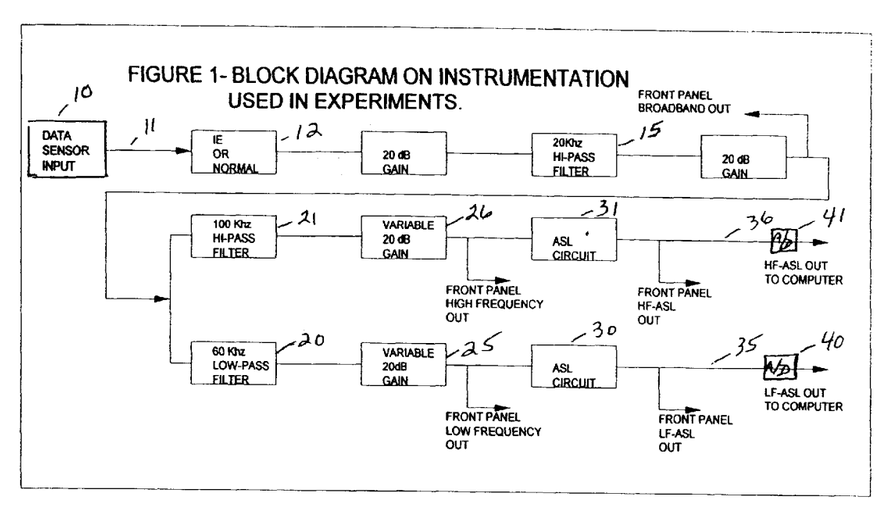
FIG. 1 is a block diagram of AE apparatus constructed in accordance with a preferred embodiment of the invention.

Referring now to FIG. 1, the transducer 10 is typically a high frequency piezoelectric transducer such as an SE-900-MWB sold by Dunegan Engineering Consultants Incorporated, Laguna Nigel, Calif. This transducer is attached to the object being tested. Scraping the surface of the object produces an acoustic emission (AE) signal at the output 11.

Figure 12:
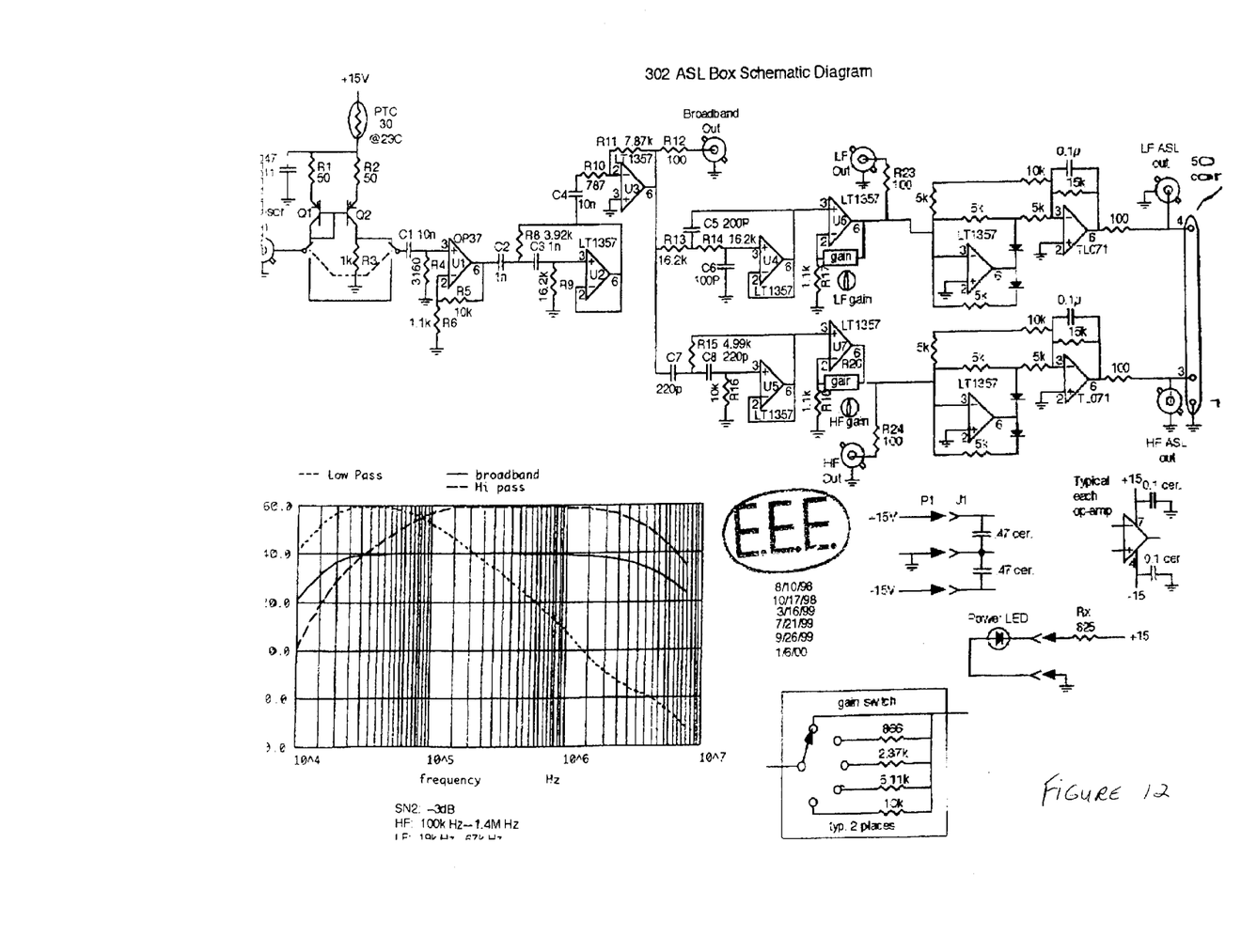
FIG. 12 is a circuit schematic for the ASL block of FIG. 1.

In the specific embodiment shown, frequencies below about 20 KHz are filtered out by filter 15. The output of this filter 15 is amplified and electronically filtered through respectively 20–60 KHz bandwidth filter 20, and 100 KHz–1 MHz bandwidth filter 21. Both filtered signals are then amplified by respective gain amplifier and put through respective averaging electronic ASL circuits 30, 31 that produce the average signal level(ASL) of the two filtered signals at their respective outputs. A circuit schematic for its ASL circuit is shown in FIG. 12. These ASL signals on 35, 36 are then inputted to respective A/D converters 40, 41 into a PC such as a laptop computer. The A/D connector 40, 41 may be already incorporated into the computer. Each signal is sampled by the A/D converters at a selected sample rate of around 10 milliseconds. The computer then divides the digitized voltage of the high frequency channel by the digitized voltage of the low frequency channel to produce a ratio designated as the HF/LF ratio. As described below, it is this ratio that allows surface roughness to be determined, without being influenced by velocity or instrumentation amplification.

Figure 2:
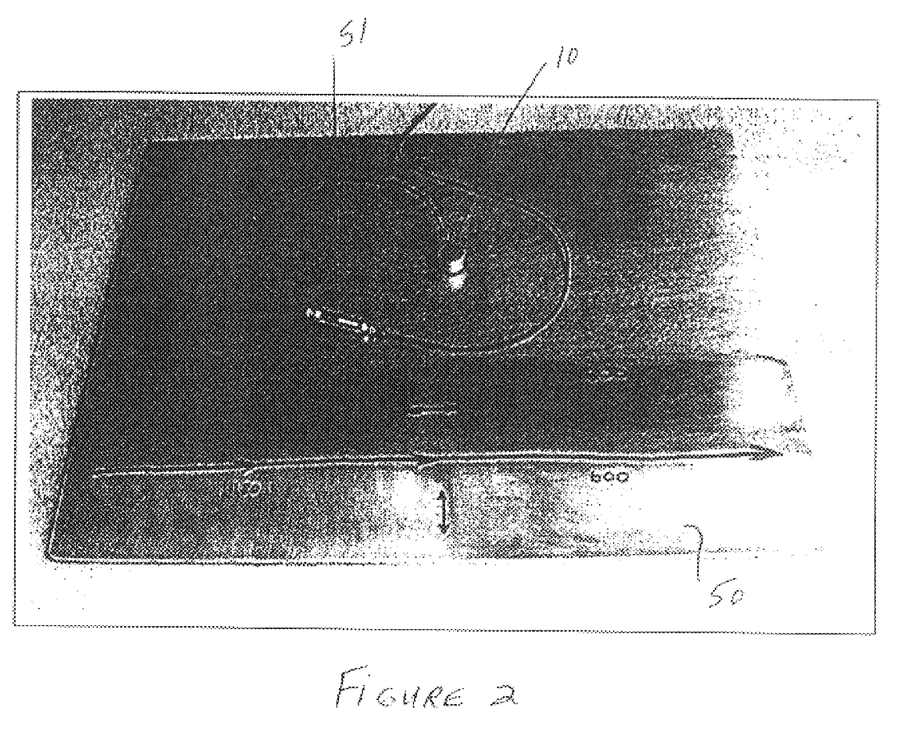
FIG. 2 illustrates an embodiment using the apparatus of FIG. 1 to measure surface roughness.

A test example using the apparatus of FIG. 1 will now be described. Referring first to FIG. 2, an aluminum plate 50 has coupled to it the SE900-MWB piezoelectric transducer 10. In the test example described below, plate 50 was abraded with two different roughness of grit (180 and 600) over an area of approximately 10 inches in length and 2 inches wide. A strip of this length was abraded with the 180 grit and immediately followed by a strip of 600 grit. In one case the surface was abraded with movement of the sandpaper along the length of the 10 inch strip with each grit size giving a 2 inch wide strip of abraded surface 20 inches long. Adjacent to this strip was an identical strip with the two grit sizes, only this time the movement of the sandpaper to form the abraded surface was 90 degrees to the movement producing the first strip. A photograph of the aluminum plate is shown in FIG. 2, showing the AE sensor (SE900-MWB) 10 and MINI-P preamplifier 51 in the center of the 500×500 mm plate of aluminum 5 mm thick. Referring again to FIG. 1, the MINI-P preamplifier 51 is part of the data sensor input block 10 and also available from Dunegan Engineering Consultants Incorporated. Block 12 in FIG. 1 represents two possible states. In the IE (Internal Electronics) state, the preamplifier is included in block 10. If it is not included, the unit 12 is in its alternate "normal" state. The small arrows show the direction of movement of the sandpaper used to create the two surfaces, while the large arrow shows the movement of the index finger of the author in contact with the abraded surfaces to produce the AE signals. Several different objects moving in contact with the abraded surfaces to produce AE signals were tried, but the best results were obtained by using the human finger.

Contact was made with the abraded surface with the index finger, starting at the 180 grit end and moving the finger along the 20 inch strip at a constant velocity. Immediately after completing the 20 inch strip, a rerun was made at a different velocity. In the same manner a run at constant velocity was made on the two adjacent strips to discover the effect of orientation of the grooves in the surface produced by the sandpaper. Another run involved moving the finger at a constant velocity on one of the strips and reproducing the same run after changing the gain of the instrumentation by 10 dB to determine the influence of instrumentation gain on the results.

During each of these runs, the HF voltage, LF voltage, Time, and Ratio of the HF/LF voltage was recorded by the instrumentation. The PC was programmed such that any one of these parameters could be observed in real time on the computer screen. After each test, the results were transferred by the computer software to an Excel spread sheet for graphical analysis. HF voltage, LF voltage, and Ratio were plotted as a function of time for each of the different conditions listed above.

Velocity Effects

Figure 3:
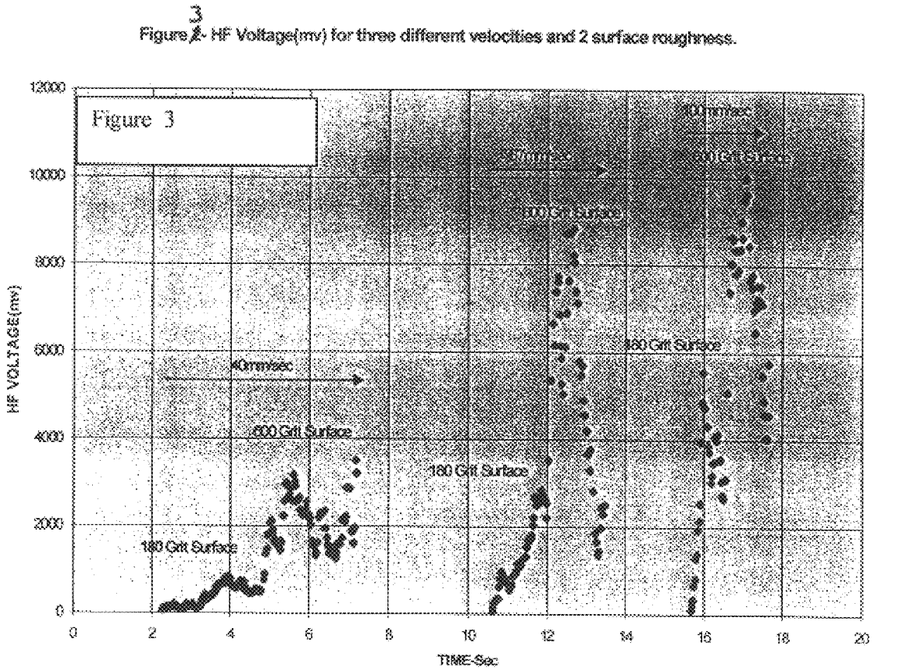
FIG. 3 shows that the high frequency ASL voltage signal for three different velocities and two surface roughnesses.

FIG. 3 shows the effects of three different velocities for the two different surface roughness on only the HF ASL voltage channel. Note that the voltage is trending higher as the velocity increases for the 600 grit surface, but shows very little increase as the velocity increases for the 180 grit surface. The drop in voltage during the last second for the 600 grit surface is due to a combination of a decrease in velocity and contact pressure created by attempting to lift the finger to prevent artifacts created when the finger goes over the edge of the plate. These results show a very high dependence of the HF voltage on velocity for the 600 grit surface, and a lesser increase as a function of velocity on the rougher surface.

Figure 4:
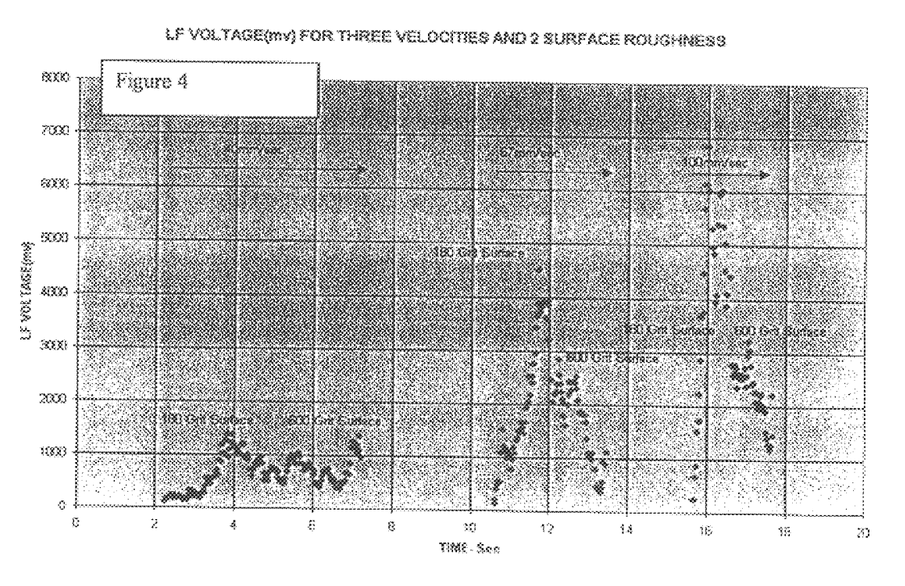
FIG. 4 shows the low frequency ASL voltage signal for the different velocities and two surface roughnesses.

FIG. 4 shows only the LF ASL voltage as a function of time for this same experiment. Note in this example just the opposite effect is present in the data. In this example a large increase in the low frequency voltage is observed as the velocity is increased for the 180 grit surface, and a lessor increase is seen in the voltage level for the 600 grit surface.

Figure 5:
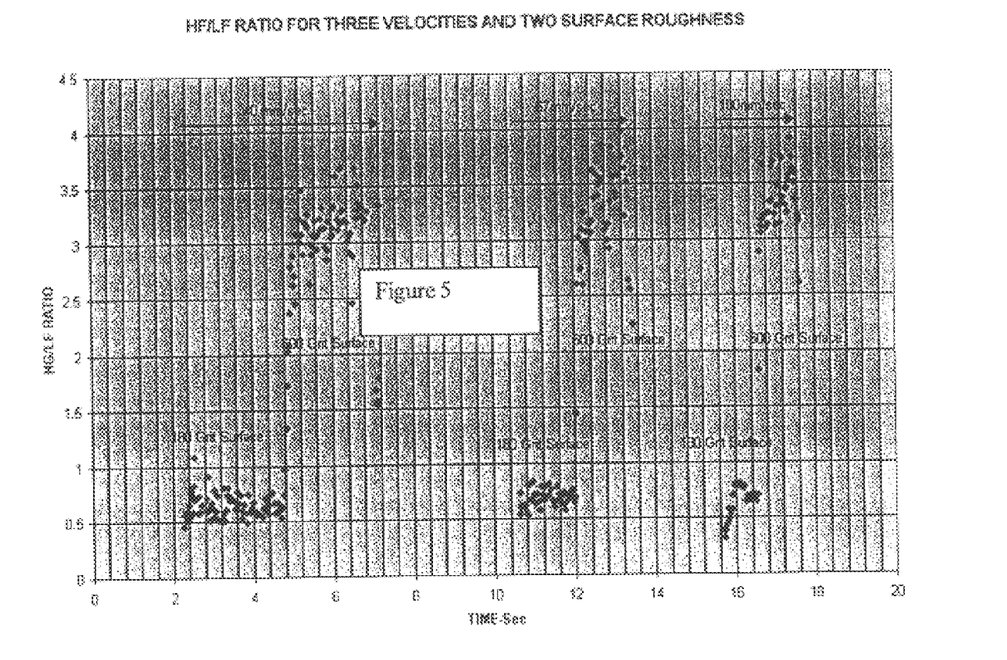
FIG. 5 shows the ratio of the high frequency ASL voltage and the low ASL frequency voltage for the three different velocities and two surface roughnesses.

FIG. 5 shows the Ratio of the HF/LF voltage calculated by the PC computer connected to the A/D circuits 40, 41 in the manner described above for the three velocities. Note that a very large difference is observed in the ratio for the two different grit sizes with no apparent dependence on the velocity of movement across the different surfaces. A smaller grid was used for the time base in order to show how quickly the ratio changes when moving from one surface condition to the other.

Orientation Effects

Another run was conducted to study the effects of moving the finger over the different roughness of the plate, parallel and perpendicular to the grooves created by the sandpaper.

Figure 6:
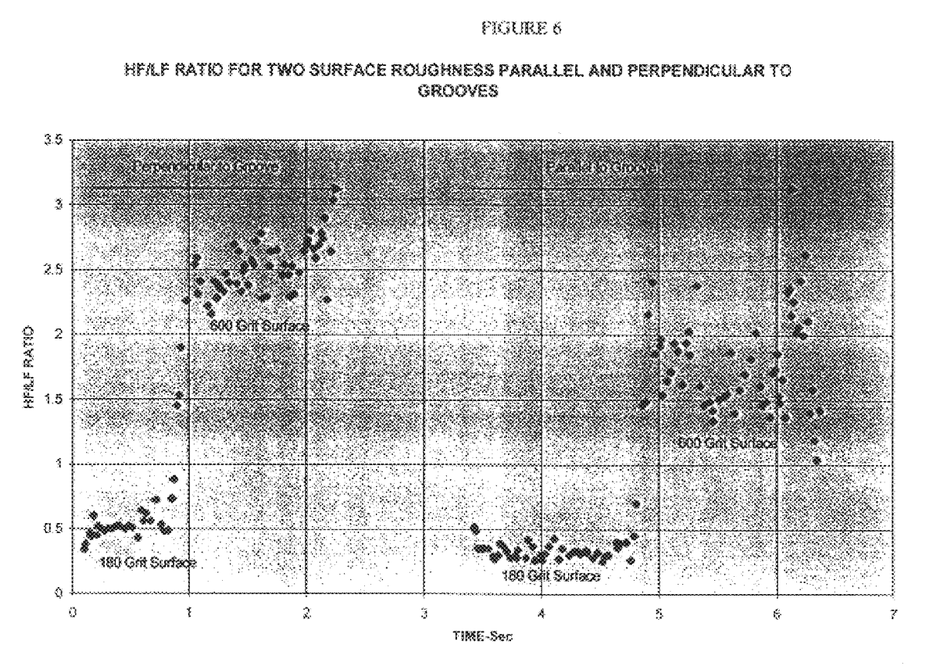
FIG. 6 illustrates the HF/LF ratio for two surface roughness parallel and perpendicular to grooves.

FIG. 6 shows these results. An attempt was made to maintain the same velocity of movement for each of these conditions, but as can be observed by the length of time required to cover the full 20 inches of the plate, the velocity for the movement parallel to the grooves in the plate was slower.

If one assumes that velocity is not a factor, as was shown in the previous figure, the data shows that orientation effects are very minimal on the rougher surface, but do appear to have an effect on the smoother surface.

Instrumentation Gain Effects

Figure 7:
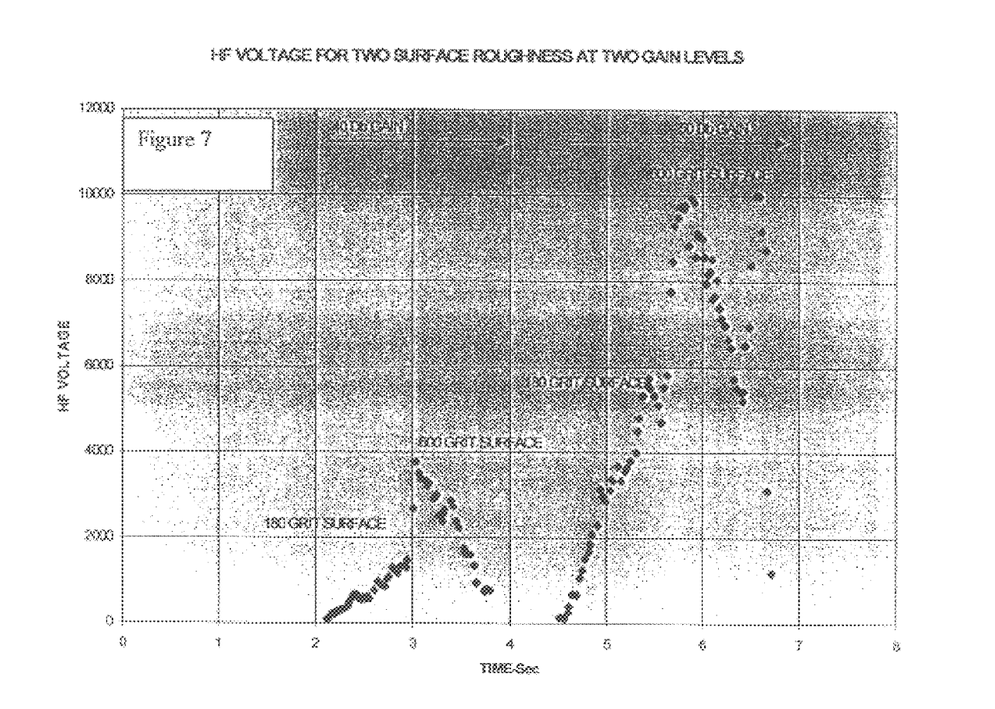
FIG. 7 illustrates the high frequency ASL voltage for two surface roughnesses at two gain levels.

This run was designed to study the effects of instrumentation gain settings on the ability of the HF/LF ratio to measure the difference between two surface roughness. FIG. 7 shows only the HF ASL voltage as a function of time for two roughness at 40 and 50 dB of instrumentation gain. Note the large difference in voltage level for the two gain settings of variable gain stages 25, 26 of FIG. 1. The drop in voltage for the 600 grit situation after reaching its peak value is due to a decrease in velocity near the edge of the plate. Although differences are observed in the HF voltage level from the two different surfaces it would be difficult to base a quantitative measure of surface roughness on such data.

Figure 8:
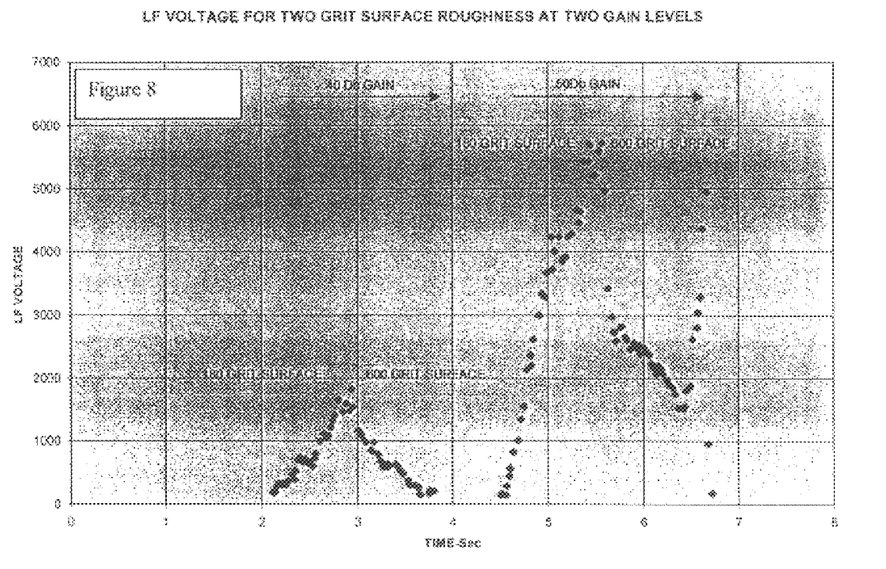
FIG. 8 illustrates the low frequency ASL voltage for two surface roughnesses at two gain levels.

FIG. 8 shows only the LF ASL voltage data from the same experiment. Here again we observe a large difference in the voltage level due to the 10 dB difference in instrumentation gain. The same drop off in voltage observed in FIG. 7 is also present in this data. Note the difference in vertical scale between FIG. 7 and FIG. 8. Some of the signals in the HF data of FIG. 7 were approaching the saturation voltage of 10 volts for the 600 grit surface.

Figure 9:
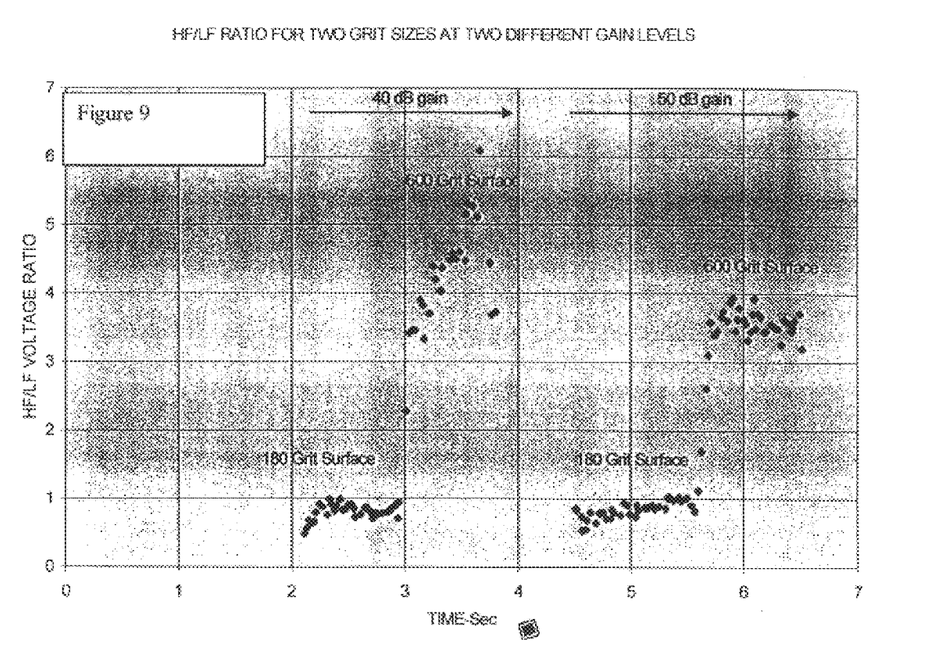
FIG. 9 illustrates the HF/LF ratio for two surface roughness at two different gain levels.

FIG. 9 shows the HF/LF ratio of the data shown in FIG. 7 and FIG. 8 produced by the apparatus described above and shown in FIG. 1. Here again we observe that taking the ratio of the high frequency to low frequency components of an AE signal provides a quantitative measure of the two surface conditions even though the instrumentation gain level was changed by a factor of 10 dB.

There is a great deal of scatter in the voltage data but considerably less scatter in the HF/LF ratio data. It appears that taking a cumulative average of the ratio data for a particular grit surface might be a better way of displaying the data. Also since only two grit surfaces were used it was decided to include a third grit surface intermediate between the 180 and 600 grit surfaces. Therefore 400 grit sandpaper was used to prepare another 10 inch strip on the aluminum plate. A run was made on each of the three surfaces and a cumulative average of the HF/LF data was calculated. This data is shown by FIG. 10.

The use of the cumulative average of all signals for each surface roughness provides a unique value for each of the three surfaces. A graph showing the relationship between HF/LF ratio and surface roughness is shown by FIG. 11. The three points selected for FIG. 11 was the final value for each of the surface roughness in FIG. 10.

Figure 10:
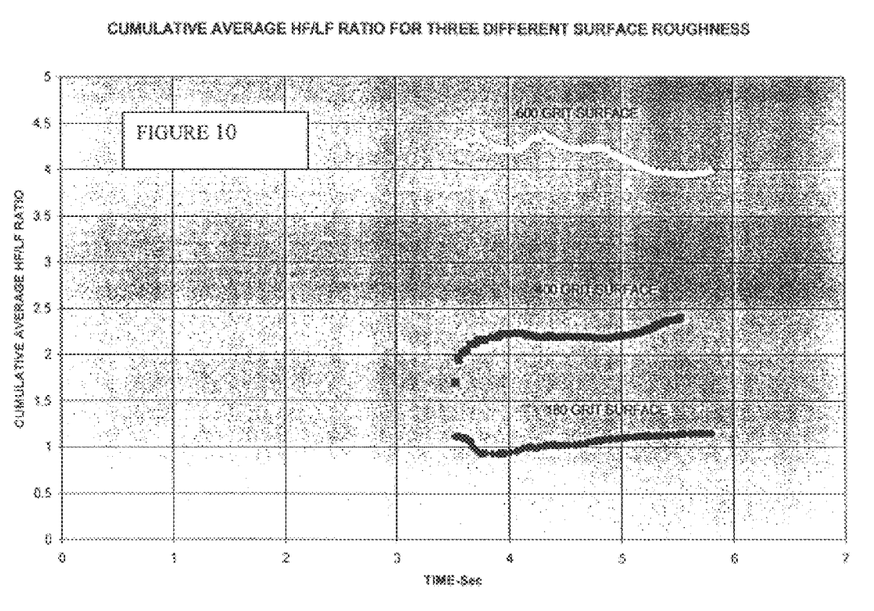
FIG. 10 illustrates the cumulative average HF/LF ratio for three different surface roughnesses.
Figure 11:
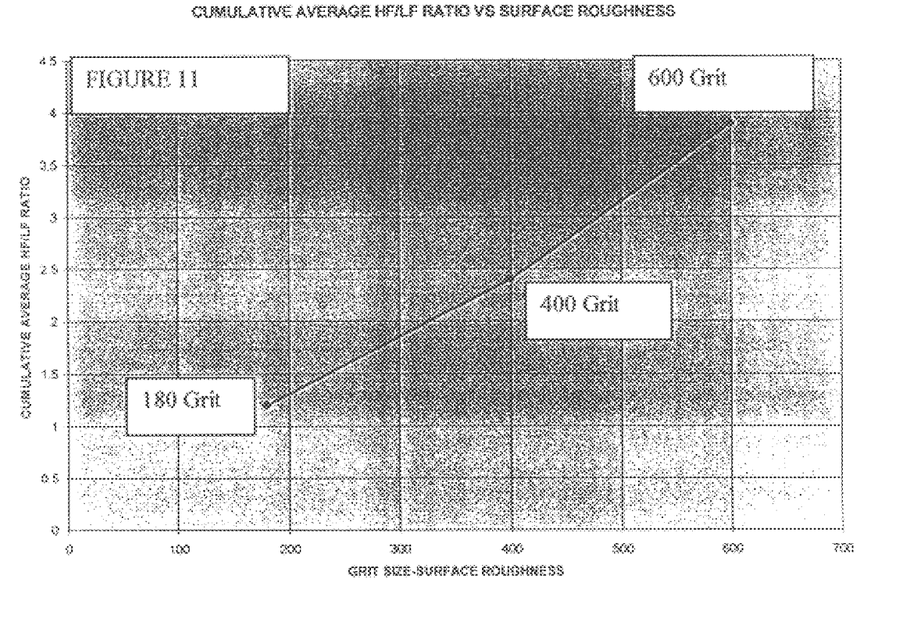
FIG. 11 illustrates the cumulative average HF/LF ratio versus surface roughness.

The data presentation shown by FIG. 10 appears to be the best way of displaying the HF/LF ratio for measuring surface roughness. The software in the instrument (AESMART 302A) is designed to show the cumulative average of the ratio data shown in FIG. 10 in real time, and a numerical value of the average of all data points for a particular run is displayed on the screen. From this value one can determine the surface roughness from the graphic in FIG. 11.

Another feature of the software in the Model 302A is a ratio filter. A value of the ratio corresponding to a desired surface roughness can be preset. This preset ratio has to be exceeded in order for any data recorded to be considered valid. In this manner the progress of metal machining, grinding, or polishing operations can be monitored until the desired surface finish is achieved.

Discussion of Experimental Results

As stated above, the use of a single RMS or ASL value of the AE signal, and subsequent analysis of the data using pattern recognition techniques or neural networks, must take into account the velocity dependence of the process and the gain of the instrumentation. FIGS. 3 and 4 show the large differences in signal amplitude produced by varying the velocity of the contact area over the surface of the part to be measured. As seen in FIG. 4, the low frequency components of the signal show a higher velocity dependence from the rougher surface and a lessor velocity dependence for the smoother surface. The opposite effect is shown from FIG. 3 for the high frequency data. There appears to be very little velocity dependence for the high frequency data from the rougher surface, but a large dependence on velocity for the smoother surface is observed. When, however, the high frequency data shown in FIG. 3 is divided by the low frequency data of FIG. 4, the HF/LF ratio is calculated. This ratio data is shown by FIG. 5 and it is observed that using the apparatus of this invention shown in FIGS. 1 and 2, there is no velocity dependence on this ratio and most of the scatter in the data disappears. The opposite effects produced on the different frequency components of the signal appear to amplify the difference seen in the ratios from the two different surface roughness and eliminate the velocity dependence.

FIG. 6 shows that there are differences observed due to orientation of the grooves in the surface. When contact movement is made perpendicular to the grooves the best separation between rough and smooth surface is observed. Contact parallel to the grooves produces a considerable amount of scatter in the high frequency data and a lower overall ratio for both surfaces.

FIG. 7 shows the dependence of the voltage from the low frequency channel for a change in instrumentation gain of 10 dB. FIG. 8 shows the change in the high frequency voltage for the same change in gain. The ratio of the HF/LF voltage shown by FIG. 9 shows that the gain dependence has no effect on the value of the ratio. This is an important advantages of the invention, since the measuring parameter is independent of the absolute amplitude of the signal. This again shows the value of taking the ratio of two frequency components of a signal rather than attempting to use the amplitude of the signal itself as a measuring parameter.

A considerable amount of scatter is observed in the voltage amplitude of the data. Much of this scatter is due to the difficulty in producing a consistent surface of a specific roughness, and maintaining a constant velocity over the 20 inches of surface tested by simple movement of the index finger on the surface. The averaging method shown by the data from three different surfaces in FIG. 10 appears to provide a solution to this problem.

Theoretical Considerations

To the inventor's knowledge there has been no published theory that would explain the results given in this report. A possible explanation for the results observed are as follows: When the finger is rubbed over the surface both Sv and Sh shear waves are created. A properly designed transducer coupled to the surface with petroleum jelly is capable of detecting both types of shear waves which are inherently high frequency in nature, and the low frequency flexure wave. The HF/LF ratio calculated is therefore the voltage due to the high frequency shear wave divided by the voltage due to the low frequency flexure wave. It is apparent from the data in FIG. 3 that the 180 grit surface produces higher voltages from the low frequency channel indicating that a higher percentage of Sv and subsequently low frequency flexure waves are produced by the rougher surface. This is supported by the drop off in voltage for the low frequency channel for signals from the smoother surface. It is postulated that the smoother surface produces a higher percentage of Sh waves that maintain their high frequency nature without mode conversion. This is supported by the higher amplitudes observed from the high frequency channel in FIG. 2 for the 600 grit surface.

APPLICATIONS OF THE INVENTION

Measurement of Surface Roughness

The example described above shows that surface roughness measurements can be made with good accuracy.

Metal Cutting

The AE transducer 10 is attached to the tool used on a lathe in a metal cutting process. A sharp tool, optimum depth of cut and optimum speed of travel should produce primarily high frequency shear waves in the tool. If the tool encounters a hard inclusion, a crack is initiated, or the tool becomes dull micro-impacts will occur which will produce low frequency flexure waves in the tool. The HF/LF ratio of the AE data should determine optimum conditions for the cutting process and alarm if conditions outside the preset ratio filter are exceeded.

Polishing

It is anticipated that results similar to the data presented in this report will result from polishing operations. As the surface becomes smoother higher ratios will result.

Grinding

It is anticipated that the same correlation can be obtained with surfaces created with a grinding wheel as opposed to sandpaper.

Head Disk Interference (HDI)

Present HDI researchers using AE techniques utilize a very small transducer and monitoring frequencies in the 500 KHz range. The low frequencies are rejected by hi-pass filtering of the AE data. As described above, utilizing the amplitude of only a high frequency signal can result in vastly different results, depending on velocity effects and instrument gain (FIG. 2, FIG. 6). It is anticipated that substantially more accurate results can be obtained in HDI studies by utilizing the HF/LF ratio produced by the apparatus of this invention which is not affected by velocity effects and instrument gain.

CONCLUSIONS

As shown and described above, this invention provides acoustic emission apparatus and methods that are significant advances in the art. By splitting the received signal into two frequency bands and taking the ratio of the high frequency to low frequency components of the voltage amplitude (HF/LF ratio) results in a parameter that can be quantitatively related to the surface roughness independent of the relative velocity between the finger and plate, and the instrumentation amplification. Variations of velocity, instrument gain, transducer placement and orientation of the grooves produced in the plate were studied. Of these four parameters studied only orientation of the grooves seemed to have a measurable effect on the HF/LF ratio data.

What is claimed is:

1. An apparatus for measuring surface roughness comprising:

a piezoelectric transducer adapted to be coupled to the surface to be tested having an output which is a broadband acoustic emission signal, a low frequency filter coupled to said broadband signal, a high frequency filter coupled to said broadband signal, a first voltage averaging circuit attached to the output of said low frequency filter, a second voltage averaging circuit attached to the output of said high frequency filter, and a computer coupled to said first and second voltage averaging circuits having an output signal which is the ratio of the high frequency averaged signal and the low frequency averaged signal, said output signal being quantitatively related to surface roughness.

2. The apparatus of claim 1, wherein said low frequency filter passes signals between about 20 KHz to 60 KHz and said high frequency filter passes signals between about 100 KHz and 1 MHz.

* * * * *